(12) United States Patent  
Kaneoka (10) Patent No.: US 9,557,377 B2  
(45) Date of Patent: Jan. 31, 2017

(54) FAULT ANALYSIS APPARATUS AND FAULT ANALYSIS METHOD

(71) Applicant: HAMAMATSU PHOTONICS K.K., Hamamatsu-shi, Shizuoka (JP)

(72) Inventor: Takayoshi Kaneoka, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 15 days.

(21) Appl. No.: 14/637,752

(22) Filed: Mar. 4, 2015

(65) Prior Publication Data

US 2015/0253241 A1 Sep. 10, 2015

Related U.S. Application Data

(60) Provisional application No. 61/948,840, filed on Mar. 6, 2014.

(51) Int. Cl.

| | | |
|---|---|---|
| *G01R 31/28* | (2006.01) | |
| *G01N 21/00* | (2006.01) | |
| *G01R 31/311* | (2006.01) | |
| *G01R 31/302* | (2006.01) | |
| *G01N 21/84* | (2006.01) | |

(52) U.S. Cl.  
CPC ............ *G01R 31/311* (2013.01); *G01R 31/28* (2013.01); *G01R 31/302* (2013.01); *G01N 21/00* (2013.01); *G01N 21/84* (2013.01)

(58) Field of Classification Search  
None  
See application file for complete search history.

(56) References Cited

U.S. PATENT DOCUMENTS

| 4,656,419 | A | * | 4/1987 | Garlick | .............. | G01R 31/2632 |
|---|---|---|---|---|---|---|
| | | | | | | 136/290 |
| 4,695,794 | A | * | 9/1987 | Bargett | ................ | G01R 31/305 |
| | | | | | | 324/750.02 |
| 5,150,043 | A | * | 9/1992 | Flesner | ................ | G01R 31/308 |
| | | | | | | 324/750.14 |
| 5,708,371 | A | * | 1/1998 | Koyama | .............. | G01R 31/311 |
| | | | | | | 324/754.23 |

(Continued)

OTHER PUBLICATIONS

Hamamatsu Photonics K.K., "Inverted Emission Microscope iPHEMOS Series," Nov. 2014, pp. 1-8.

*Primary Examiner* — Tri Ton  
*Assistant Examiner* — Jarreas C Underwood  
(74) *Attorney, Agent, or Firm* — Drinker Biddle & Reath LLP (57) ABSTRACT

A fault analysis apparatus is an apparatus for measuring a reaction of a semiconductor device having a wiring extending in two directions orthogonal to each other. The fault analysis apparatus comprises a laser light source that outputs laser light, a control unit that sets a scan direction which is a direction of scanning an irradiation position of the laser light in the semiconductor device, a laser scanner that scans the laser light according to the scan direction, an electric signal detector that measures the reaction of the semiconductor device to the laser light and outputs a measured value, and an image processing unit that creates a two-dimensional map according to the irradiation position and the measured value. The control unit sets the scan direction such that the scan direction intersects the wiring extending directions at an angle greater than 0° but smaller than 90°.

16 Claims, 7 Drawing Sheets

(56) References Cited

U.S. PATENT DOCUMENTS

| | | | | | |
|---|---|---|---|---|---|
| 5,966,019 | A | * | 10/1999 | Borden | G01R 31/311 |
| | | | | | 257/E21.53 |
| 6,005,400 | A | * | 12/1999 | Thundat | G01R 31/2656 |
| | | | | | 257/E21.531 |
| 6,320,396 | B1 | * | 11/2001 | Nikawa | H01L 22/12 |
| | | | | | 257/E21.53 |
| 6,477,265 | B1 | * | 11/2002 | Sheng | G06T 7/0002 |
| | | | | | 250/491.1 |
| 6,888,956 | B2 | * | 5/2005 | Muramatsu | G06K 9/00899 |
| | | | | | 340/5.83 |
| 8,319,503 | B2 | * | 11/2012 | Negishi | G01R 1/18 |
| | | | | | 324/613 |

* cited by examiner

(b) Measured Value

Irradiation Position

Fig.7

FAULT ANALYSIS APPARATUS AND FAULT ANALYSIS METHOD

This application claims the benefit of U.S. Provisional Application No. 61/948,840 filed Mar. 6, 2014, which is incorporated by reference herein in its entirety.

BACKGROUND OF THE INVENTION

Field of the Invention

The present invention relates to a fault analysis apparatus and a fault analysis method for a semiconductor.

Related Background Art

As a method for analyzing a fault of a semiconductor device, a method is known, in which laser light is irradiated to the semiconductor device so as to extract an electric signal from the semiconductor device, thereby analyzing the fault. Examples of such a method include OBIRCH (Optical Beam Induced Resistance Change) measurement which measures a change in resistance value accompanying heat caused by irradiation with laser light or the like (see U.S. Pat. No. 6,320,396), OBIC (Optical Beam Induced Current) measurement which measures a photovoltaic current generated by irradiation with laser light, and DALS (Dynamic Analysis by Laser Stimulation) which measures a reaction to a stimulation caused by laser light in a state where a test pattern is inputted to the semiconductor device.

SUMMARY OF THE INVENTION

The fault analysis apparatus in accordance with one aspect of the present invention is a fault analysis apparatus for irradiating a semiconductor device having a wiring extending in two directions orthogonal to each other with light and measuring a reaction of the semiconductor device thereto, the fault analysis apparatus comprising a light source configured to output light for irradiating the semiconductor device; a scan setting unit configured to set a scan direction which is a direction of scanning a light irradiation position in the semiconductor device; a light scanner configured to scan the light according to the scan direction; a detector electrically connected to the semiconductor device and configured to measure the reaction of the semiconductor device irradiated with the light and output a measured value; and a map creation unit configured to create a two-dimensional map two-dimensionally mapping a fault position according to the irradiation position and the measured value; while the scan setting unit sets the scan direction such that the scan direction intersects the wiring extending directions at an angle greater than 0° but smaller than 90°.

This fault analysis apparatus measures an electric reaction such as a current or voltage value, for example, of a semiconductor device which is irradiated with light. The measured value becomes smaller in a defective part whose electric resistance is higher than that in the other parts because of, for example, inferior wiring, than in other part. Wiring areas in the semiconductor device yield a measured value lower than that in other areas made of a silicon material or the like, though not so low as that in the defective part. Therefore, when the scan direction of the light irradiation position lies along a wiring direction, measured values become smaller in both of the defective part in the wiring area and the other part in the wiring area. This makes it difficult to specify the defective part from differences in measured values. For securely specifying the defective part, not one but a plurality of scan directions have conventionally been employed.

In this regard, the wiring of the semiconductor device extends in two directions orthogonal to each other in the fault analysis apparatus in accordance with one aspect of the present invention. The scan direction of the light irradiation position in the semiconductor device is set such that the scan direction intersects the wiring directions of the semiconductor device at an angle greater than 0° but smaller than 90°. Therefore, the scan direction of the light irradiation position does not lie along (is not parallel to) the wiring directions. As a consequence, when there is a defective part in the wiring area, for example, the other part in the wiring area and the defective part in the wiring area are hard to become continuous irradiation positions. Hence, a scan from one direction can clarify a difference between a measured value of the defective part and that of the other part and thus can easily specify the defective part from the difference between the measured values. As in the foregoing, specifying the defective part from one scan direction can simplify the measurement and reduce the measurement time.

In the fault analysis apparatus in accordance with one aspect of the present invention, the scan setting unit may set the scan direction such that the scan direction intersects the wiring extending directions at about 45°. When the scan direction is set so as to intersect the wiring extending directions at 45°, the defective part in the wiring area and the other part in the wiring area are harder to become continuous irradiation positions, whereby the defective part can be specified securely by a scan from one direction.

In the fault analysis apparatus in accordance with one aspect of the present invention, the map creation unit may create the two-dimensional map by performing a coordinate transformation taking account of the scan direction. While the scan direction has a predetermined gradient with respect to the wiring directions, the coordinate transformation taking account of the gradient can create a two-dimensional map having two axes in the wiring directions, thereby making it easier to specify a fault.

In the fault analysis apparatus in accordance with one aspect of the present invention, the map creation unit may create the two-dimensional map by superimposing an image determined from the irradiation position and the measured value onto an image representing a structure of the semiconductor device. Superimposing the former image onto the latter image makes it easier to specify the fault.

The fault analysis apparatus in accordance with another aspect of the present invention is a fault analysis apparatus for irradiating a semiconductor device with light and measuring a reaction of the semiconductor device thereto, the fault analysis apparatus comprising a light source configured to output light for irradiating the semiconductor device; a stage configured to support the semiconductor device and move the semiconductor device in two directions orthogonal to each other; a scan setting unit configured to set a scan direction which is a direction of scanning a light irradiation position in the semiconductor device; a light scanner configured to scan the light according to the scan direction; a detector electrically connected to the semiconductor device and configured to measure a reaction of the semiconductor device irradiated with the light and output a measured value; and a map creation unit configured to create a two-dimensional map two-dimensionally mapping a fault position according to the irradiation position and the measured value; while the scan setting unit sets the scan direction such that the scan direction intersects the directions in which the stage moves the semiconductor device at an angle other than 0°, 90°, 180°, and 270°.

In the fault analysis apparatus in accordance with another aspect of the present invention, the scan setting unit may set the scan direction such that the scan direction intersects the directions in which the stage moves the semiconductor device at about 45°.

The fault analysis method in accordance with still another aspect of the present invention is a fault analysis method of measuring a reaction of a semiconductor device having a wiring extending in two directions orthogonal to each other by irradiating the semiconductor device with light, the method comprising the steps of mounting the semiconductor device on a stage, scanning a light irradiation position in the semiconductor device such that the scan direction intersects the wiring extending directions at a predetermined angle, measuring a reaction of the semiconductor device irradiated with the light and outputting a measured value, and creating a two-dimensional map two-dimensionally mapping a fault position according to the irradiation position and the measured value.

In the fault analysis method in accordance with still another aspect of the present invention, in the step of scanning the light irradiation position, the light irradiation position may be scanned such that the scan direction which is a direction of scanning the irradiation position of the light intersects the wiring extending directions at about 45°.

In the fault analysis method in accordance with still another aspect of the present invention, in the step of creating the two-dimensional map, the two-dimensional map may be created by performing a coordinate transformation taking account of the scan direction.

In the fault analysis method in accordance with still another aspect of the present invention, in the step of creating the two-dimensional map, the two-dimensional map may be created by superimposing an image determined from the irradiation position and the measured value onto an image representing a structure of the semiconductor device.

DESCRIPTION OF THE EMBODIMENTS

In the following, preferred embodiments of the present invention will be explained in detail with reference to the drawings. In the drawings, the same or equivalent parts will be referred to with the same signs, while omitting their overlapping descriptions.

First Embodiment

Figure 1:
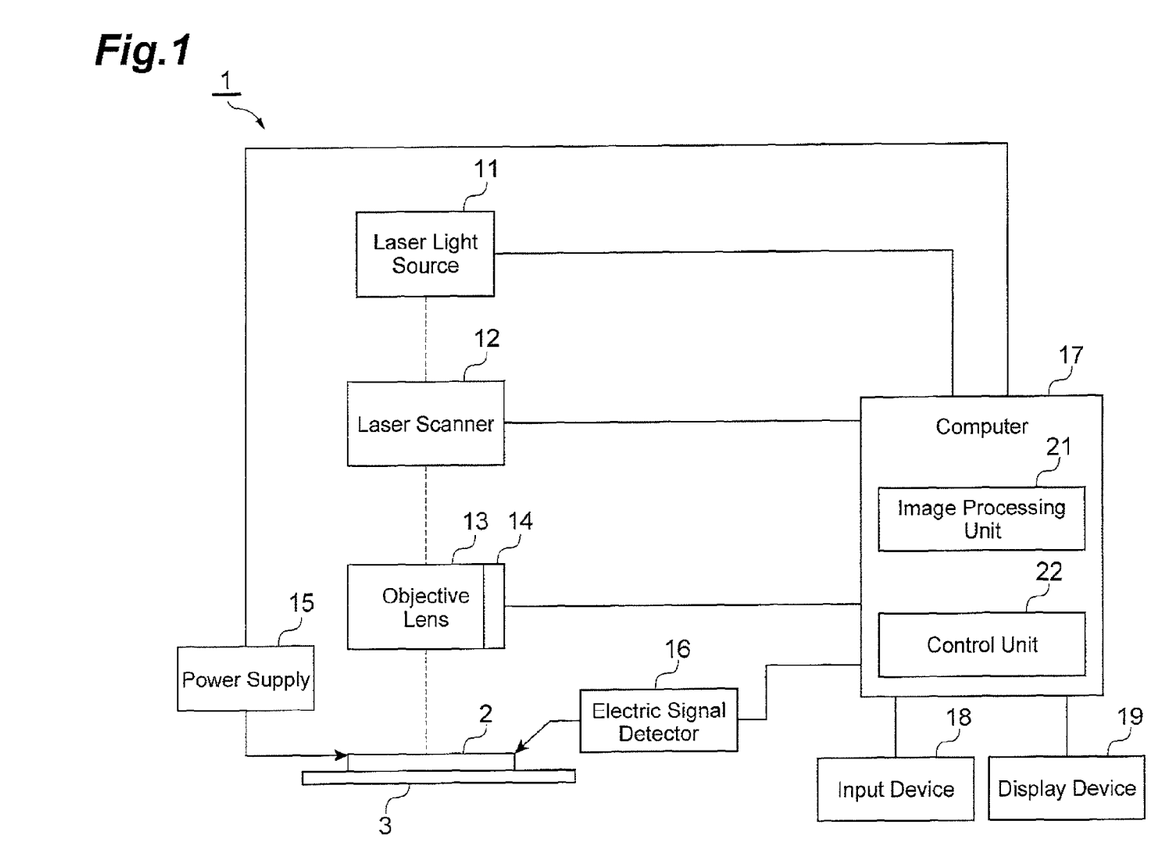
FIG. 1 is a structural diagram of the fault analysis apparatus in accordance with a first embodiment of the present invention.

FIG. 1 is a structural diagram of the fault analysis apparatus in accordance with the first embodiment of the present invention. As illustrated in FIG. 1, the fault analysis apparatus 1 in accordance with the first embodiment is an apparatus for inspecting a semiconductor device 2, which is a device under test (DUT), by specifying a location where an abnormality occurs therein, for example. Specifically, the fault analysis apparatus 1 is an apparatus for measuring a reaction of the semiconductor device 2 by irradiating the semiconductor device 2 with light.

The fault analysis apparatus 1 is a fault analysis apparatus for analyzing a fault by OBIRCH or OBIC measurement. The OBIRCH measurement is a technique for measuring a change in resistance value accompanying heat or the like generated when the semiconductor device is irradiated with laser light. The OBIC measurement is a technique for measuring a photovoltaic current generated when the semiconductor device is irradiated with laser light.

Examples of the semiconductor device 2 include integrated circuits having p-n junctions such as transistors (e.g., circuits of small scale integration (SSI), medium scale integration (MSI), large scale integration (LSI), very large scale integration (VLSI), ultra large scale integration (VLSI), and giga-scale integration (GSI)), large-current/high-voltage MOS transistors and bipolar transistors, and power devices. The semiconductor device 2 may also be one which can apply modulation caused by heat to a substrate. The semiconductor device 2 is electrically connected to a power supply 15 and allows the latter to apply a fixed voltage or current thereto. However, it is not always necessary for the power supply 15 to apply the voltage or current.

The semiconductor device 2 is mounted on and supported by a stage 3. The stage 3 moves in two directions orthogonal to each other. The two directions (moving directions) orthogonal to each other in which the stage 3 moves may be explained in the following as directions X, Y. When the stage 3 moves in the directions X, Y, so does the semiconductor device 2 mounted on the stage 3. A wiring (line) of the semiconductor device 2 extends in two directions orthogonal to each other. The directions of the wiring (wiring directions) are unambiguously determined when the semiconductor device 2 is mounted on the stage 3 and coincide with the above-mentioned directions X, Y. Therefore, the wiring directions of the semiconductor device 2 may be explained in the following as the directions X, Y.

The fault analysis apparatus 1 is equipped with a laser light source (light source) 11. The laser light source 11 generates and outputs coherent light (laser light) for irradiating the semiconductor device 2. The semiconductor device 2 is irradiated with the laser light outputted from the laser light source 11. In the OBIRCH measurement, the laser light source 11 outputs laser light in such a wavelength band as to pass through the semiconductor device 2. That is, in the OBIRCH measurement in the case where the semiconductor device 2 is made of silicon, for example, the laser light source 11 outputs laser light in a wavelength band which is longer than 1100 nm, preferably at about 1300 nm. Thus, in the OBIRCH measurement, the laser light source 11 outputs laser light in such the wavelength band as to pass through the semiconductor device 2, whereby a photovoltaic current can be restrained from occurring. In the OBIC measurement, it is necessary for the laser light source 11 to output light in such a wavelength region as to be absorbed by the semiconductor device 2. Therefore, the laser light source 11 outputs light having a wavelength of 1100 nm or shorter. The light source is explained to be the laser light source in this embodiment, but the light source is not limited to the laser light source and may be any of light sources which output coherent light, such as LED (Light Emitting Diode), SLD (Super Luminescent Diode), or ASE (Amplified Spontaneous Emission) light sources. The laser light outputted from the laser light source 11 is guided to a laser scanner 12 through a polarization-maintaining single-mode optical fiber for probe light (not depicted).

The laser scanner 12 is a light scanning unit that receives the light from the laser light source 11 and scans a laser light irradiation position in the semiconductor device 2 in a predetermined direction. Specifically, the laser scanner 12 has a scan head and a lens system and is constructed by a light scanning element of a galvano-mirror or polygon-mirror optical system, for example. The laser scanner 12 may also modulates the amplitude or phase of the light with a spatial light modulator. The laser light guided to the laser scanner 12 is converged by an objective lens 13 onto the semiconductor device 2. The light guided to the laser scanner 12 forms an image at a predetermined irradiation position in the semiconductor device 2. The objective lens 13 has low- and high-magnification objective lenses which are switchable by a lens turret (objective lens switcher) 14. The lens turret 14 is controlled by a computer 17. The lens turret 14 may manually switch the objective lens 13.

The laser scanner 12 scans the laser light irradiation position according to a preset scan direction. The scan direction is a direction in which the laser light irradiation direction in the semiconductor device 2 is scanned. The above term "preset" means that it is set beforehand by the computer (scan setting unit) 17 electrically connected to the laser scanner 12. Not only the scan direction but also the irradiation position scanned by the laser scanner 12 is controlled by the computer 17 (as will be explained later in detail). The reaction of the semiconductor device 2 irradiated with the laser light is measured by an electric signal detector (measurement unit) 16.

The electric signal detector 16 measures the reaction of the semiconductor device 2 irradiated with the laser light and outputs a measured value. In the OBIRCH measurement, for example, the electric signal detector 16 measures a change in electric resistance of the semiconductor device 2 accompanying the heat generated by irradiation with the laser light. In the OBIRCH measurement, the power supply 15 applies a fixed voltage or current to the semiconductor device 2. In the case where a fixed voltage is applied from the power supply 15, the semiconductor device 2 changes its electric resistance when irradiated with the laser light. The electric signal detector 16 measures a change in current value accompanying the change in electric resistance of the semiconductor device 2. The electric signal detector 16 may measure the change in current value either directly or indirectly through measurement of a magnetic field or change in magnetic field occurring together with the change in electric resistance. In the case where a fixed current is applied from the power supply 15, the voltage value of the semiconductor device 2 changes together with the electric resistance thereof. The electric signal detector 16 measures a change in voltage value of the semiconductor device 2 accompanying the change in electric resistance thereof. The electric signal detector 16 may measure the change in voltage value either directly or indirectly through measurement of an electric field or change in electric field occurring together with the change in electric resistance. In the OBIC measurement, on the other hand, the electric signal detector 16 measures the reaction of the semiconductor device 2 by determining a current or change in current in the semiconductor device 2 accompanying a photovoltaic current generated by irradiation with the laser light. The electric signal detector 16 may measure the current value or change in current value either directly or indirectly through measurement of a magnetic field or change in magnetic field accompanying the generation of the photovoltaic current. The electric signal detector 16 outputs the measured value of the semiconductor device 2 to the computer 17.

An example of the computer 17 is a PC. The computer 17 has an image processing unit 21 and a control unit 22. Various kinds of information can be inputted to the computer 17 from an input device 18 according to user operations. An example of the input device 18 is a keyboard. The image outputted from the computer 17 is displayed on a display device 19.

The control unit 22 controls the laser light source 11, laser scanner 12, lens turret 14, power supply 15, electric signal detector 16, input device 18, and display device 19. The control unit 22 sets the scan direction of the laser scanner 12. The control unit 22 sets the scan direction such that the scan direction intersects the wiring directions of the semiconductor device 2 (i.e., moving directions of the stage 3, ditto in the following) at a predetermined angle. That is, the control unit 22 sets the scan direction such that the scan direction is not parallel to but obliquely intersects the wiring directions. For example, the control unit 22 sets the scan direction such that the scan direction intersects the directions X, Y, which are wiring directions, at an angle greater than 0° but smaller than 90°. Alternatively, the control unit 22 sets the scan direction such that the scan direction intersects the directions X, Y, which are wiring directions, at an angle other than 0°, 90°, 180°, and 270°. Preferably, the control unit 22 sets the scan direction such that the scan direction intersects the directions X, Y, which are wiring directions, at an angle within the range of 30° to 60°. More preferably, the control unit 22 sets the scan direction such that the scan direction intersects the directions X, Y, which are wiring directions, at an angle of about 45°. The term "about 45°" includes not only just 45° but also a margin on the order of ±5°, i.e., the range of 40° to 50°, for example. The other angles explained in this embodiment are also meant to include a margin on the order of ±5° as mentioned above even when the term "about" is not used.

The control unit 22 also controls the laser light irradiation position of the laser scanner 12. The control unit 22 specifies the laser light irradiation position for the laser scanner 12. The laser light irradiation position is specified by two-dimensional positional information indicated by positions (coordinate positions) in the scan direction and a direction orthogonal thereto. The control unit 22 acquires the measured value of the semiconductor device 2 with respect to the laser light as outputted to the electric signal detector 16. The control unit 22 outputs the irradiation position, the measured value at the irradiation position, and the scan direction to the image processing unit 21.

Figure 2:
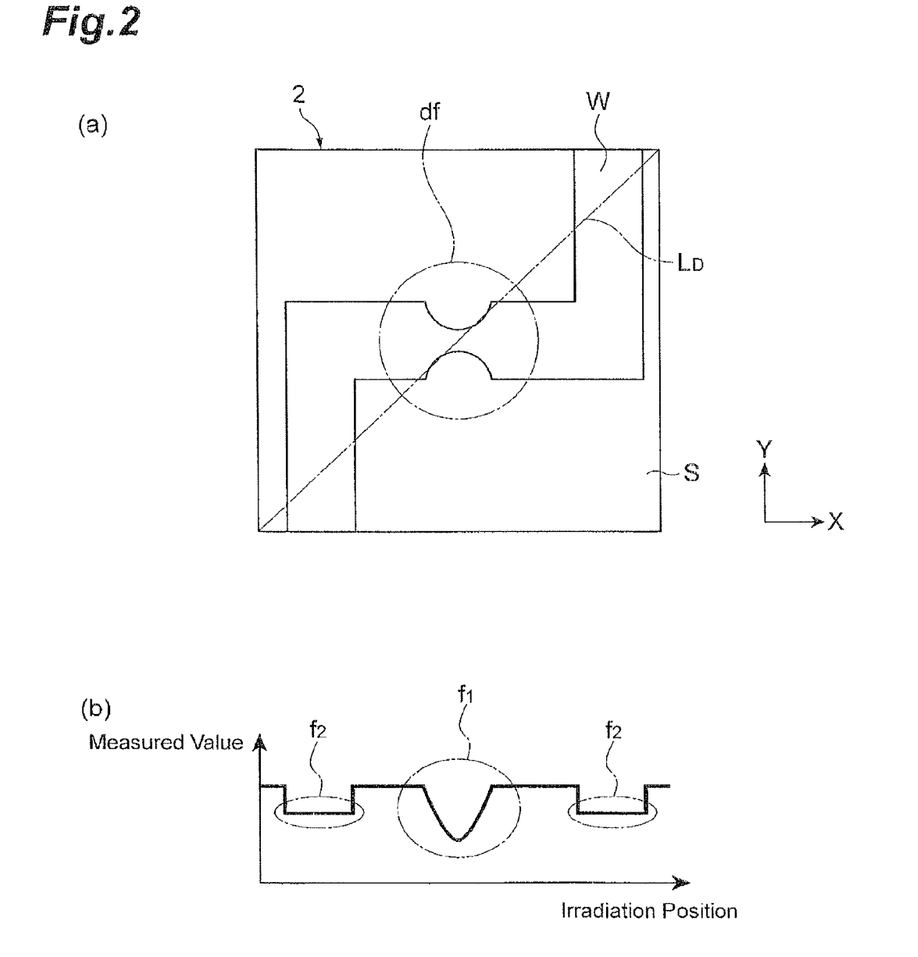
FIG. 2 is a set of diagrams for explaining how to analyze a fault when the scan direction is at 45°.

FIG. 2 is a set of diagrams for explaining how to analyze a fault when the scan direction is at 45°. The following explanation is premised on the OBIRCH measurement. An example illustrated in FIG. 2(a) represents a silicon part S and a wiring W made of a metal in the semiconductor device 2. The wiring W extends in the two directions X, Y orthogonal to each other. In this state, the control unit 22 sets a scan direction $L_D$ such that the scan direction $L_D$ intersects the directions X, Y, which are wiring directions, at 45°. The laser scanner 12 irradiates the semiconductor device 2 with laser light according to the scan direction $L_D$ set by the control unit 22.

The image processing unit (map creation unit) 21 creates a two-dimensional map according to the irradiation position and the measured value outputted to the control unit 22. An example of the two-dimensional map is an image two-dimensionally mapping a position specified as a fault, while using the directions X, Y, which are wiring directions, as two axes. FIG. 2(b) is a chart indicating the irradiation position on one axis and the measured value on the other axis. In the example illustrated in FIG. 2, a part of the wiring W is a defective part df formed thinner than designed. Such a defective part df yields an electric resistance higher than that in the other part, whereby a measured value $f_1$, which is a current value, for example, is lower than the other measured values. This makes it possible to specify the irradiation position concerning the defective part df. An image created in the OBIRCH measurement (OBIRCH image) has a contrast corresponding to the measured value such that a part having a lower measured value is displayed darker than its surroundings.

Figure 3:
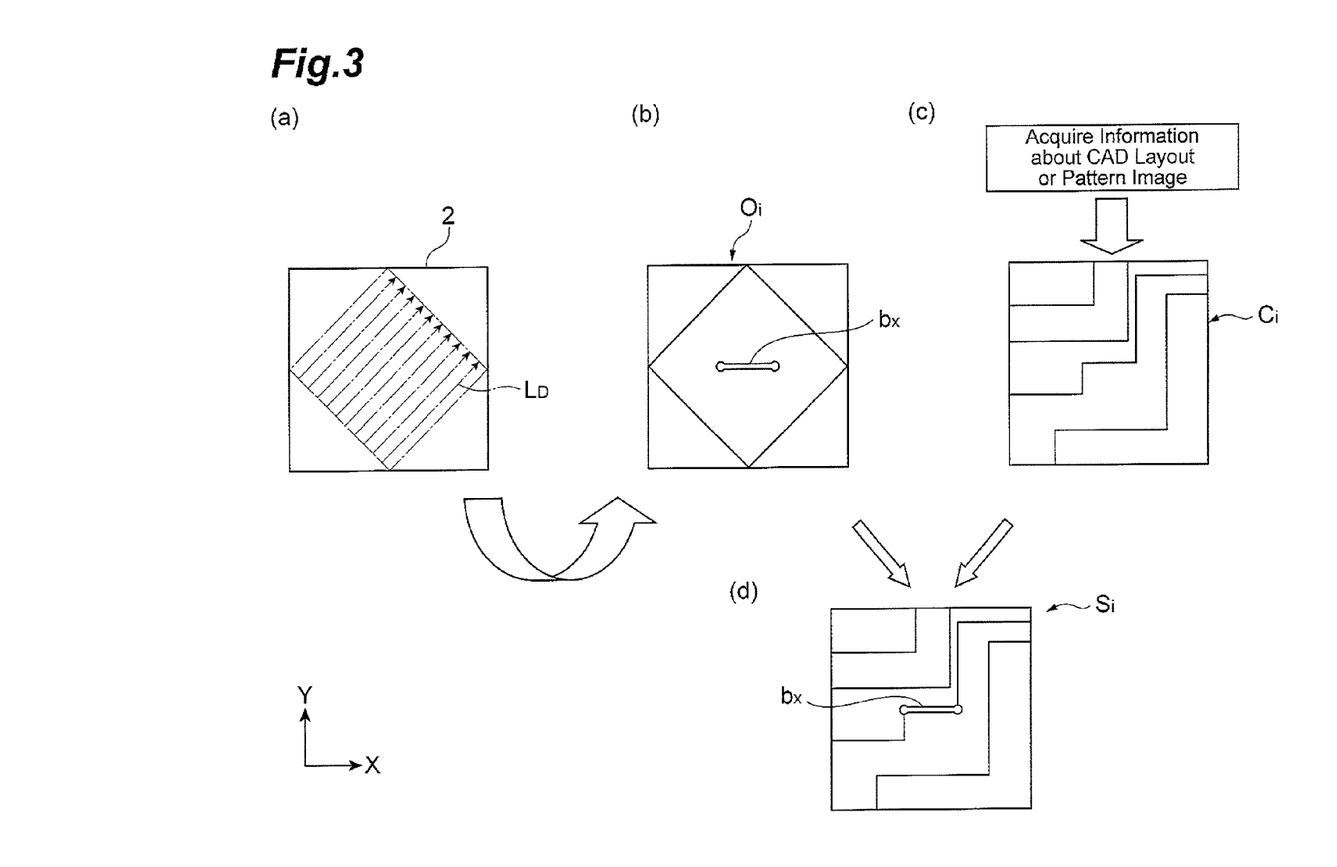
FIG. 3 is a set of diagrams for explaining how to create a two-dimensional map.

In the example illustrated in FIG. 2, the scan direction $L_D$ is a direction intersecting the directions X, Y, which are wiring directions, at 45° as illustrated in FIG. 3(a). Therefore, by performing a coordinate transformation taking account of the gradient of the scan direction $L_D$ (a coordinate transformation based on the angle at which the scan direction $L_D$ intersects the directions X, Y that are wiring directions), the image processing unit 21 can create an OBIRCH image $O_i$ in which two axes are the directions X, Y (see FIG. 3(b)). In the OBIRCH image $O_i$ illustrated in FIG. 3(b), a fault location $b_x$ is displayed appropriately along the direction X that is a wiring direction.

The image processing unit 21 may further create an image (superimposed image $S_i$, see FIG. 3(d)) in which the above-mentioned OBIRCH image $O_i$ after the coordinate transformation is superimposed on an image indicating an actual structure of the semiconductor device 2, e.g., a CAD (computer aided design) layout image $C_i$ (see FIG. 3(c)) stored beforehand in the computer 17 or a pattern image such as an LSM (Laser Scanning Microscope) image or two-dimensional image of the semiconductor device 2. The image indicating the actual structure of the semiconductor device 2 is an image representing a structure of the semiconductor device 2 such as arrangement and forms of wiring and elements such as transistors in the semiconductor device 2, while two axes of each of the two-dimensionally displayed CAD layout image $C_i$ and pattern image coincide with the directions X, Y that are wiring directions. The two-dimensional map includes both of the OBIRCH image $O_i$ after the coordinate transformation and the superimposed image $S_i$. The image processing unit 21 causes the display unit 19 to display thus created two-dimensional map.

Figure 4:
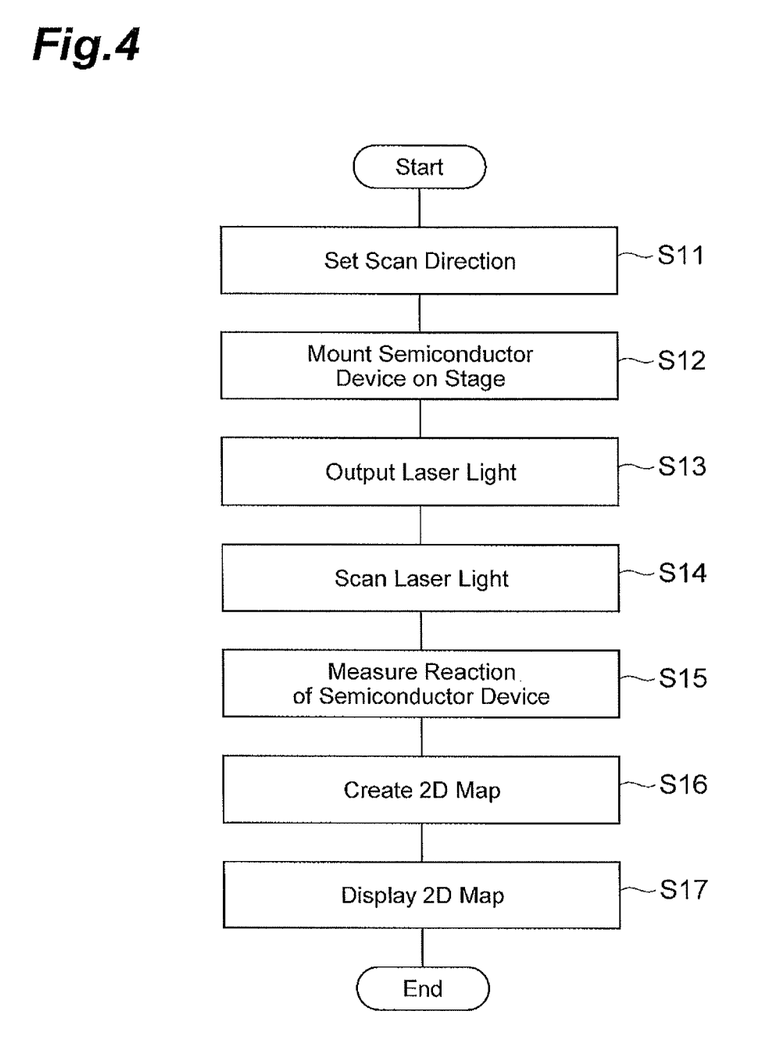
FIG. 4 is a flowchart illustrating a fault analysis process.

A flow of a method of analyzing a fault in the semiconductor device 2 by the fault analyzing apparatus 1 will now be explained with reference to FIG. 4.

First, the control unit 22 of the computer 17 sets a scan direction of the laser scanner 12 (step S11). Specifically, the scan direction is set such as to intersect the wiring directions of the semiconductor device 2 at 45°, for example. Subsequently, the semiconductor device 2 is mounted on and supported by the stage 3 (step S12). The step S12 of mounting the semiconductor device 2 on the stage 3 may also be performed simultaneously with or before the step S11 of setting the scan direction.

Next, the laser light source 11 outputs laser light (step S13). Subsequently, the laser scanner 12 scans the laser light irradiation position according to the scan direction set by the control unit 22 (step S14). Then, the electric signal detector 16 measures a reaction of the semiconductor device 2 irradiated with the laser light (step S15). The control unit 22 outputs the irradiation position and the measured value at the irradiation position together with the scan direction to the image processing unit 21 of the computer 17.

Thereafter, the image processing unit 21 creates a two-dimensional map. Specifically, the OBIRCH image $O_i$, superimposed image $S_i$, and the like in which two axes are the directions X, Y, which are wiring directions, are created. Finally, the display device 19 displays the two-dimensional map. While it is necessary for the laser light to be scanned over a plurality of scan lines in order to create a two-dimensional map, a measured reaction may be displayed as needed for each scan line having completed the measurement of the reaction of the semiconductor device, so as to create the two-dimensional map.

As explained in the foregoing, the fault analysis apparatus 1 measures an electric reaction such as a current or voltage value, for example, of the semiconductor device 2 irradiated with laser light. The measured value becomes smaller in a defective part whose electric resistance is higher than that in the other parts because of, for example, inferior wiring, than that in other part. Wiring areas in the semiconductor device 2 yield a measured value lower than that in other areas made of a silicon material or the like, though not so low as that in the defective part.

Figure 5:
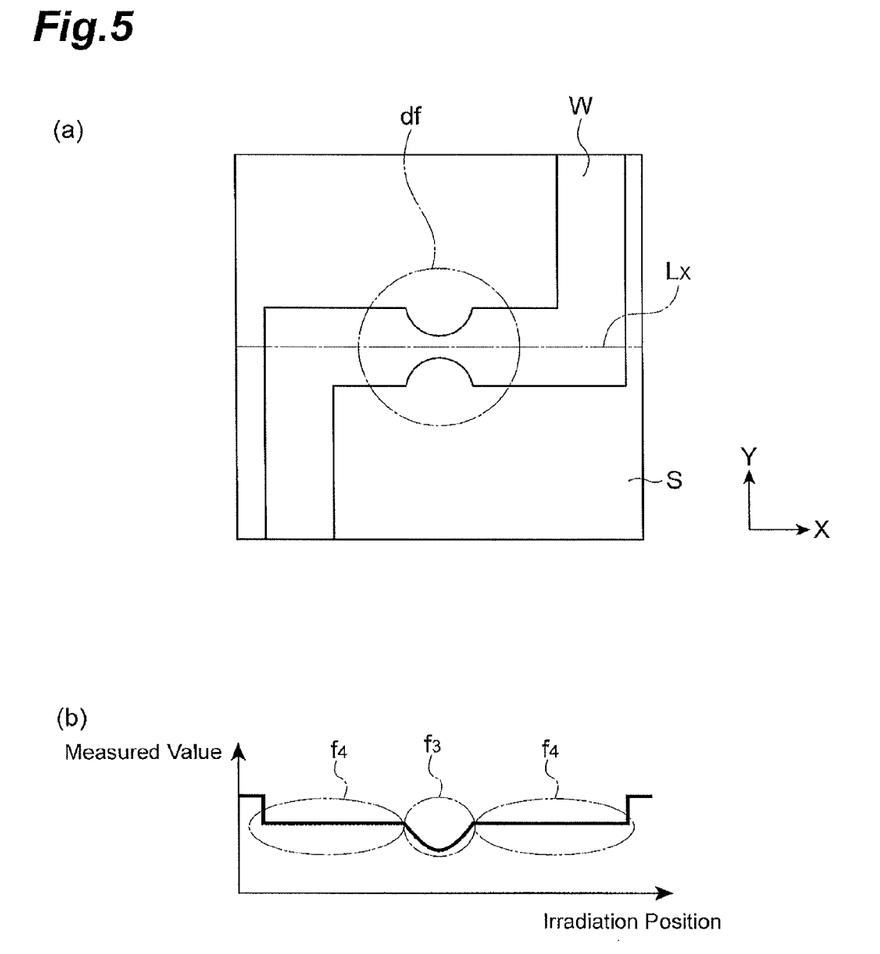
FIG. 5 is a set of diagrams for explaining a fault analysis in accordance with a comparative example.
Figure 6:
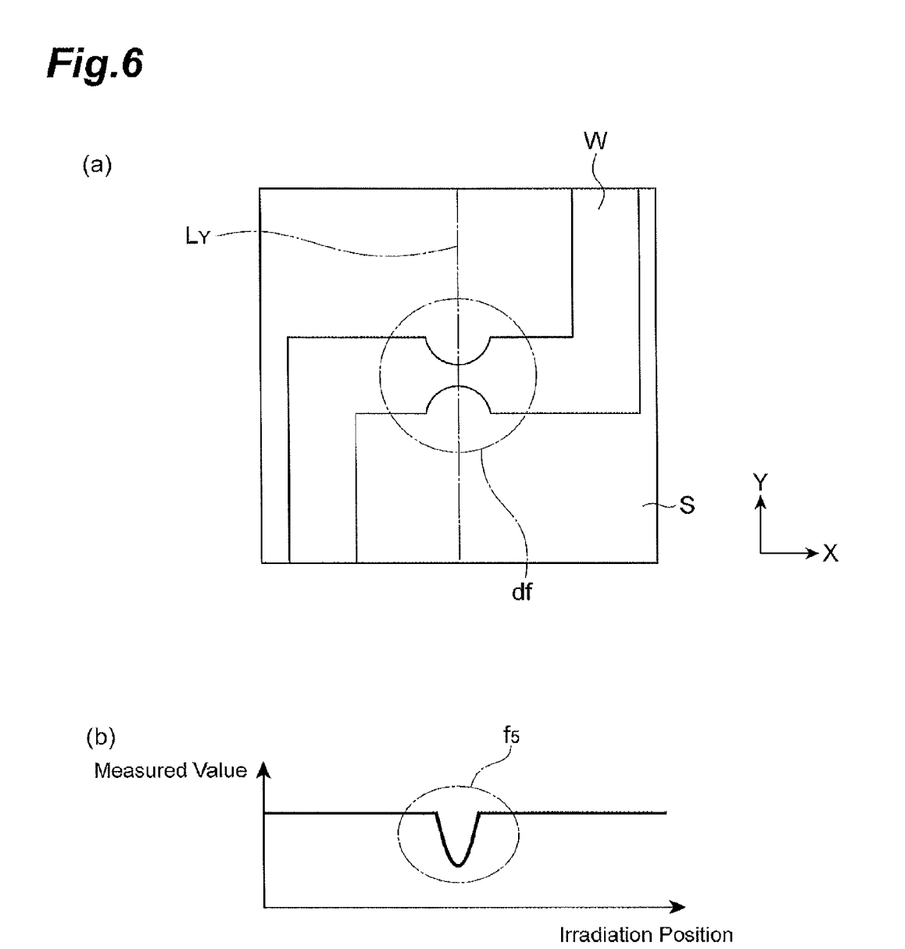
FIG. 6 is a set of diagrams for explaining a fault analysis in accordance with a comparative example.

Fault analysis methods in accordance with comparative examples will be explained with reference to FIGS. 5 and 6. The comparative examples illustrated in FIGS. 5 and 6 set their scan directions of the laser light irradiation position along the wiring directions (directions X, Y) in which the wiring W extends. A defective part df exists on a portion of the wiring W extending in the direction X in the two wiring directions orthogonal to each other. When a scan direction $L_X$ along the direction X in the wiring directions is employed as illustrated in FIG. 5(a) in this case, a measured value $f_4$ in the case where the irradiation direction is located on the wiring W and a measured value $f_3$ in the defective part df are measured continuously and both become smaller as illustrated in FIG. 5(b). In this case, the defective part is hard to specify from the difference between the measured values. This makes it necessary for the fault analysis method in accordance with the comparative example to perform irradiation in a scan direction $L_Y$ along the direction Y as illustrated in FIG. 6 in addition to the irradiation in the scan direction $L_X$.

In this regard, the scan direction $L_D$ in the fault analysis apparatus 1 in accordance with the embodiment is set such as to intersect the directions X, Y, which are wiring directions, at an angle greater than 0° but smaller than 90°. Therefore, the scan direction $L_D$ of the laser light irradiation position does not lie along (is not parallel to) the directions X, Y that are wiring directions. As a consequence, when the defective part df exists in the wiring W, for example, the other part in the wiring W and the defective part df in the wiring W are hard to become continuous irradiation positions. Hence, even when both of a measured value $f_2$ in the case where the irradiation direction is located on the wiring W and the measured value $f_1$ in the defective part df become smaller, a difference between the measured values can be clarified as illustrated in FIG. 2(b), and the defective part df can easily be specified from the difference between the measured values. As in the foregoing, specifying the defective part from one scan direction can simplify the measurement and reduce the measurement time.

The control unit 22 of the computer 17 may set the scan direction such that the scan direction intersects the wiring directions at about 45°. When the scan direction is set such as to intersect the wiring directions at about 45°, the defective part df in the wiring W and the other part in the wiring W are harder to become continuous irradiation positions, whereby the defective part df can be specified securely by a scan from one direction.

The image processing unit 21 of the computer 17 may create the two-dimensional map by performing a coordinate transformation taking account of the scan direction. While the scan direction has a predetermined gradient with respect to the wiring directions, the coordinate transformation taking account of the gradient can create a two-dimensional map having two axes in the wiring directions X, Y, thereby making it easier to specify a fault.

When the image processing unit 21 superimposes the OBIRCH image $O_i$ after the coordinate transformation onto an image indicating the structure of the semiconductor device 2, e.g., the CAD layout image $C_i$ or a pattern image, a fault can be specified more easily.

Second Embodiment

Figure 7:
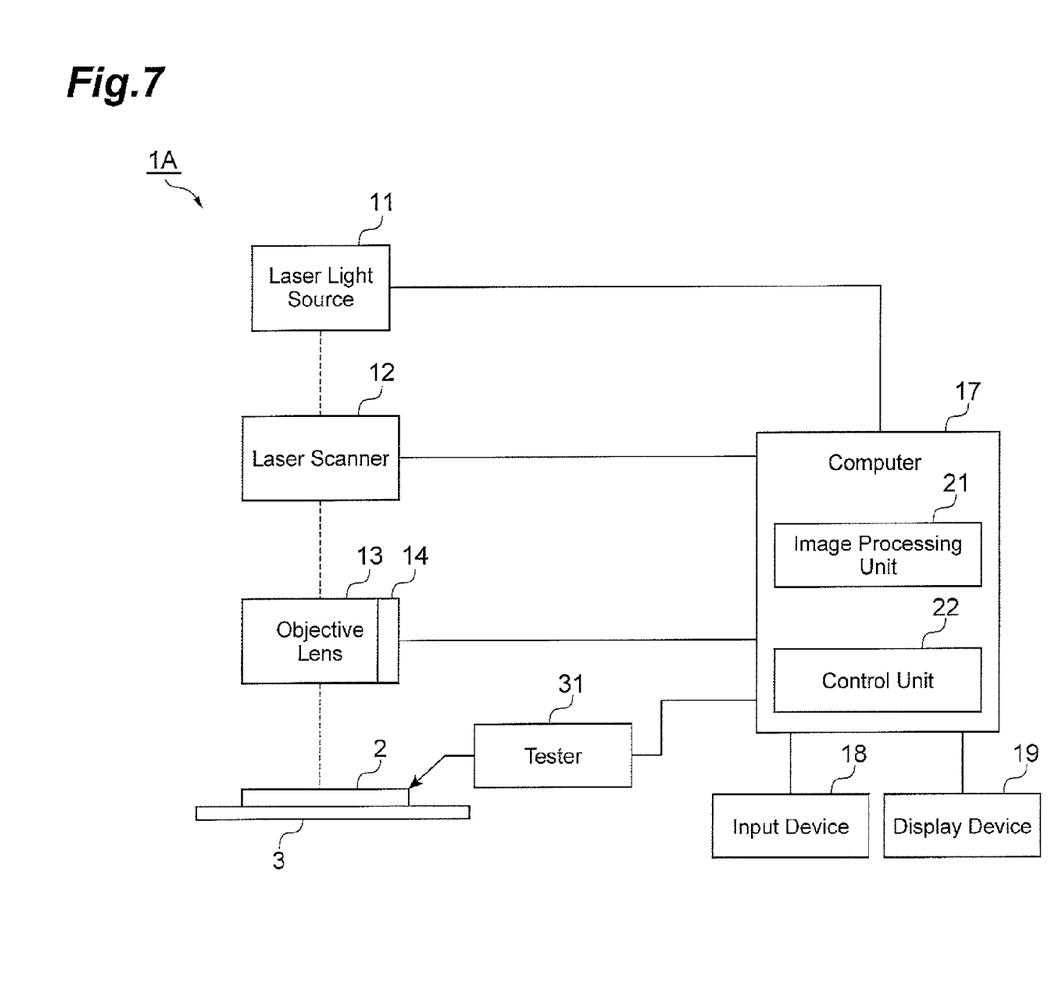
FIG. 7 is a structural diagram of the fault analysis apparatus in accordance with a second embodiment of the present invention.

A fault analysis apparatus 1A in accordance with the second embodiment will now be explained in detail with reference to FIG. 7. FIG. 7 is a structural diagram of the fault analysis apparatus 1A in accordance with the second embodiment. In this embodiment, differences from the former embodiment will mainly be explained.

The fault analysis apparatus 1A is a fault analysis apparatus for analyzing a fault by DALS measurement. The DALS measurement is a technique which measures a reaction of a semiconductor device irradiated with laser light while a test pattern is inputted to the semiconductor device. As illustrated in FIG. 7, the fault analysis apparatus 1A in accordance with this embodiment uses a tester 31 as a measurement unit in place of the electric signal detector 16 in the fault analysis apparatus 1. The tester 31 feeds the semiconductor device 2 with an operation pulse signal (test pattern) corresponding to a predetermined driving action. When fed with the test pattern, the semiconductor device 2 is placed in operation. The tester 31 monitors the operation state (Pass/Fail) of the semiconductor device 2.

In the state where the test pattern is inputted from the tester 31, the semiconductor device 2 is irradiated with laser light from the laser light source 11. The laser light is in such a wavelength region (at a wavelength longer than 1100 nm) that it is not absorbed by the semiconductor device 2. When irradiated with the laser light in such a wavelength region, the operation state of the semiconductor device 2 changes because of heating (laser heating) caused by the laser light irradiation in defective parts concerning wiring failures such as voids and transistors having specific defects. The tester 31 acquires a signal concerning the change in the operation state. The image processing unit 21 of the computer 17 creates a two-dimensional map according to the signal acquired by the tester 31, so as to specify a fault location. Thus, the fault analysis apparatuses 1A, 1 are common in that the scan direction of the laser scanner 12 is about 45°, for example, while being different from each other in terms of the technique for measuring the reaction of the semiconductor device.

Though embodiments of the present invention are explained in the foregoing, the present invention is not limited thereto. For example, the fault analysis is not required to be performed by the OBIRCH, OBIC, or DALS measurement as explained in the foregoing, but may be conducted by any of other techniques which can acquire information about the reaction of the semiconductor device by irradiation with light.

What is claimed is:

1. An apparatus for measuring a reaction of a semiconductor device having a wiring extending in two directions orthogonal to each other, the apparatus comprising:
   a light source configured to output light;
   a computer configured to set a scan direction which is a direction of scanning an irradiation position of the light in the semiconductor device;
   a light scanner electrically coupled to the computer and configured to scan the light according to the scan direction; and
   a detector electrically coupled to the computer and configured to measure the reaction of the semiconductor device irradiated with the light and output a measured value,
   wherein the computer sets the scan direction such that the scan direction intersects the wiring extending directions at an angle greater than 0° but smaller than 90° and creates a two-dimensional map indicating the reaction of the semiconductor device according to the irradiation position and the measured value by performing a coordinate transformation according to at least an angle of intersection between the scan direction and the wiring extending directions, and
   the reaction is a change in current value or voltage value.

2. The apparatus according to claim 1, wherein the computer sets the scan direction such that the scan direction intersects the wiring extending directions at about 45°.

3. The apparatus according to claim 1, wherein the computer creates the two-dimensional map by superimposing an image determined from the irradiation position and the measured value onto an image representing a structure of the semiconductor device.

4. An apparatus for measuring a reaction of a semiconductor device, the apparatus comprising:
   a light source configured to output light;
   a stage configured to support the semiconductor device and move the semiconductor device in two directions orthogonal to each other;
   a computer configured to set a scan direction which is a direction of scanning an irradiation position of the light in the semiconductor device;
   a light scanner electrically coupled to the computer and configured to scan the light according to the scan direction; and
   a detector electrically coupled to the computer and configured to measure the reaction of the semiconductor device irradiated with the light and output a measured value,
   wherein the computer sets the scan direction such that the scan direction intersects the directions in which the stage moves the semiconductor device at an angle other than 0°, 90°, 180°, and 270°, and creates a two-dimensional map indicating the reaction of the semiconductor device according to the irradiation position and the measured value by performing a coordinate transformation according to at least an angle of intersection between the scan direction and the directions in which the stage moves the semiconductor device, and
   the reaction is a change in current value or voltage value.

5. The apparatus according to claim 4, wherein the computer sets the scan direction such that the scan direction intersects the directions in which the stage moves the semiconductor device at about 45°.

6. The apparatus according to claim 4, wherein the computer creates the two-dimensional map by superimposing an image determined from the irradiation position and the measured value onto an image representing a structure of the semiconductor device.

7. A method of measuring a reaction of a semiconductor device having a wiring extending in two directions orthogonal to each other by irradiating the semiconductor device with light, the method comprising the steps of:
setting an angle of intersection between the two wiring extending directions of the semiconductor device supported by a stage and a scan direction which is a direction of scanning an irradiation position of the light;
scanning the light irradiation position in the semiconductor device;
measuring the reaction of the semiconductor device irradiated with the light and outputting a measured value; and
creating a two-dimensional map indicating the reaction of the semiconductor device according to the irradiation position and the measured value,
wherein the two-dimensional map is created by performing a coordinate transformation according to at least the angle, and
the reaction is a change in current value or voltage value.

8. The method according to claim 7, wherein the angle is other than 0°, 90°, 180°, and 270°.

9. The method according to claim 7, wherein the angle is greater than 0° but smaller than 90°.

10. The method according to claim 9, wherein the angle is about 45°.

11. The method according to claim 7, wherein the two-dimensional map is created by superimposing an image determined from the irradiation position and the measured value onto an image representing a structure of the semiconductor device.

12. An apparatus for measuring a reaction of a semiconductor device having a wiring extending in two directions orthogonal to each other by irradiating the semiconductor device with light, the apparatus comprising:
a stage configured to support the semiconductor device;
a computer configured to set an angle of intersection between the two wiring extending directions of the semiconductor device and a scan direction which is a direction of scanning an irradiation position of the light;
a light scanner electrically coupled to the computer and configured to scan the light irradiation position in the semiconductor device according to the angle; and
a detector electrically coupled to the computer and configured to measure the reaction of the semiconductor device irradiated with the light and outputs a measured value,
wherein the computer creates a two-dimensional map indicating the reaction of the semiconductor device according to the irradiation position and the measured value by performing a coordinate transformation according to at least the angle, and
the reaction is a change in current value or voltage value.

13. The apparatus according to claim 12, wherein the angle is other than 0°, 90°, 180°, and 270°.

14. The apparatus according to claim 12, wherein the angle is greater than 0° but smaller than 90°.

15. The apparatus according to claim 14, wherein the angle is about 45°.

16. The apparatus according to claim 12, wherein the computer creates the two-dimensional map by superimposing an image determined from the irradiation position and the measured value onto an image representing a structure of the semiconductor device.

* * * * *